US010835194B2

United States Patent
Sandoval

(10) Patent No.: US 10,835,194 B2
(45) Date of Patent: Nov. 17, 2020

(54) MOVABLE X-RAY BUCKY ASSEMBLY

(71) Applicant: Jennifer Sandoval, Wahneta, FL (US)

(72) Inventor: Jennifer Sandoval, Wahneta, FL (US)

(*) Notice: Subject to any disclaimer, the term of this patent is extended or adjusted under 35 U.S.C. 154(b) by 0 days.

(21) Appl. No.: 16/288,698

(22) Filed: Feb. 28, 2019

(65) Prior Publication Data

US 2020/0275899 A1 Sep. 3, 2020

(51) Int. Cl.
*A61B 6/00* (2006.01)
*A61B 6/04* (2006.01)

(52) U.S. Cl.
CPC .......... *A61B 6/4435* (2013.01); *A61B 6/4464* (2013.01)

(58) Field of Classification Search
CPC .......................... A61B 6/4435; A61B 6/4644
See application file for complete search history.

(56) References Cited

U.S. PATENT DOCUMENTS

| 4,807,273 | A | | 2/1989 | Haendle | |
|---|---|---|---|---|---|
| 5,023,899 | A | | 6/1991 | Ohlson | |
| 5,917,883 | A | * | 6/1999 | Khutoryansky | ......... A61B 6/08 378/116 |
| 6,722,783 | B2 | | 4/2004 | Jackson, Sr. | |
| 6,950,492 | B2 | | 9/2005 | Besson | |
| 8,333,308 | B2 | | 12/2012 | Maginness | |
| 8,755,490 | B2 | | 6/2014 | Takamura | |
| 9,245,658 | B2 | | 1/2016 | Desaute | |
| 9,711,251 | B2 | | 7/2017 | Lee | |
| 2005/0220273 | A1 | * | 10/2005 | Ueffinger | ............. A61B 6/4441 378/197 |
| 2007/0140436 | A1 | * | 6/2007 | Perry | ................... A61B 6/4233 378/197 |
| 2013/0235983 | A1 | * | 9/2013 | Okuno | ................. A61B 6/4464 378/197 |
| 2018/0214100 | A1 | * | 8/2018 | Kumar | ................... A61B 6/466 |
| 2019/0159740 | A1 | * | 5/2019 | Van Ammel | ........... A61B 6/589 |

FOREIGN PATENT DOCUMENTS

WO     WO2011138632     11/2011

* cited by examiner

*Primary Examiner* — Mark R Gaworecki

(57) ABSTRACT

A movable X-ray bucky assembly includes an X-ray track unit that is mounted to a ceiling of an X-ray room. The X-ray track unit includes a positioning rail that is slidable along a lateral axis of the X-ray track unit. An X-ray bucky mount is movably coupled to the positioning rail and the X-ray bucky mount is movable along a longitudinal axis of the positioning rail. Thus, the X-ray bucky mount can be positioned at a plurality of locations in the X-ray room. An X-ray detection panel is pivotally coupled to the X-ray bucky mount. Thus, the X-ray detection panel can be positioned adjacent to a patient regardless of the position of the patient within the X-ray room. In this way an X-ray image can be taken of the patient when the patient is not able to stand in front of a conventional wall mounted X-ray detection panel.

6 Claims, 3 Drawing Sheets

MOVABLE X-RAY BUCKY ASSEMBLY

CROSS-REFERENCE TO RELATED APPLICATIONS

Statement Regarding Federally Sponsored Research or Development

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION (1) Field of the Invention (2) Description of Related Art Including Information Disclosed Under 37 CFR 1.97 and 1.98

The disclosure and prior art relates to movable bucky devices and more particularly pertains to a new movable bucky device for movably coupling an X-ray detection panel to an existing X-ray track unit.

BRIEF SUMMARY OF THE INVENTION

An embodiment of the disclosure meets the needs presented above by generally comprising an X-ray track unit that is mounted to a ceiling of an X-ray room. The X-ray track unit includes a positioning rail that is slidable along a lateral axis of the X-ray track unit. An X-ray bucky mount is movably coupled to the positioning rail and the X-ray bucky mount is movable along a longitudinal axis of the positioning rail. Thus, the X-ray bucky mount can be positioned at a plurality of locations in the X-ray room. An X-ray detection panel is pivotally coupled to the X-ray bucky mount. Thus, the X-ray detection panel can be positioned adjacent to a patient regardless of the position of the patient within the X-ray room. In this way an X-ray image can be taken of the patient when the patient is not able to stand in front of a conventional wall mounted X-ray detection panel.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
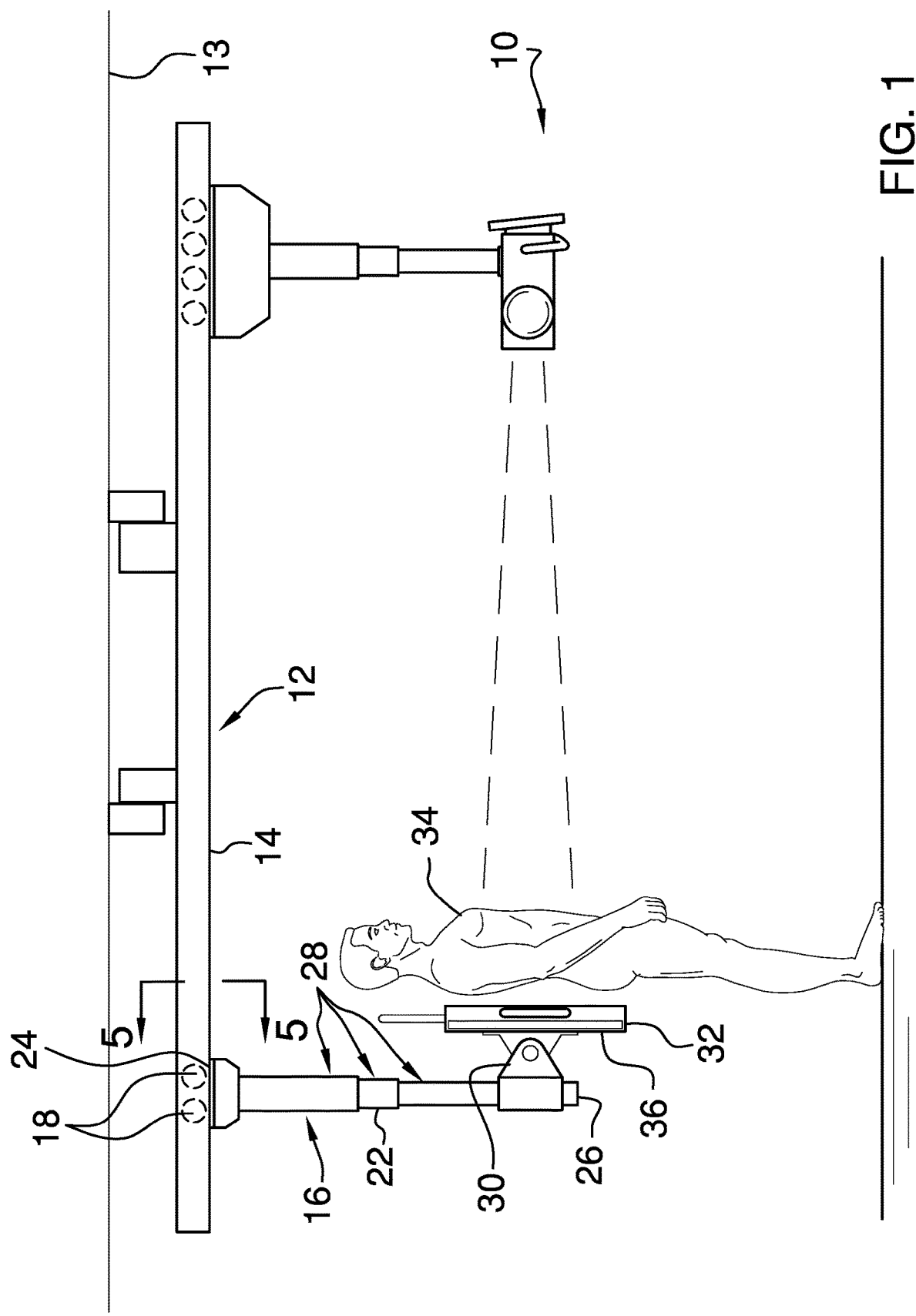
FIG. 1 is a perspective in-use view of a movable X-ray bucky assembly according to an embodiment of the disclosure.
Figure 3:
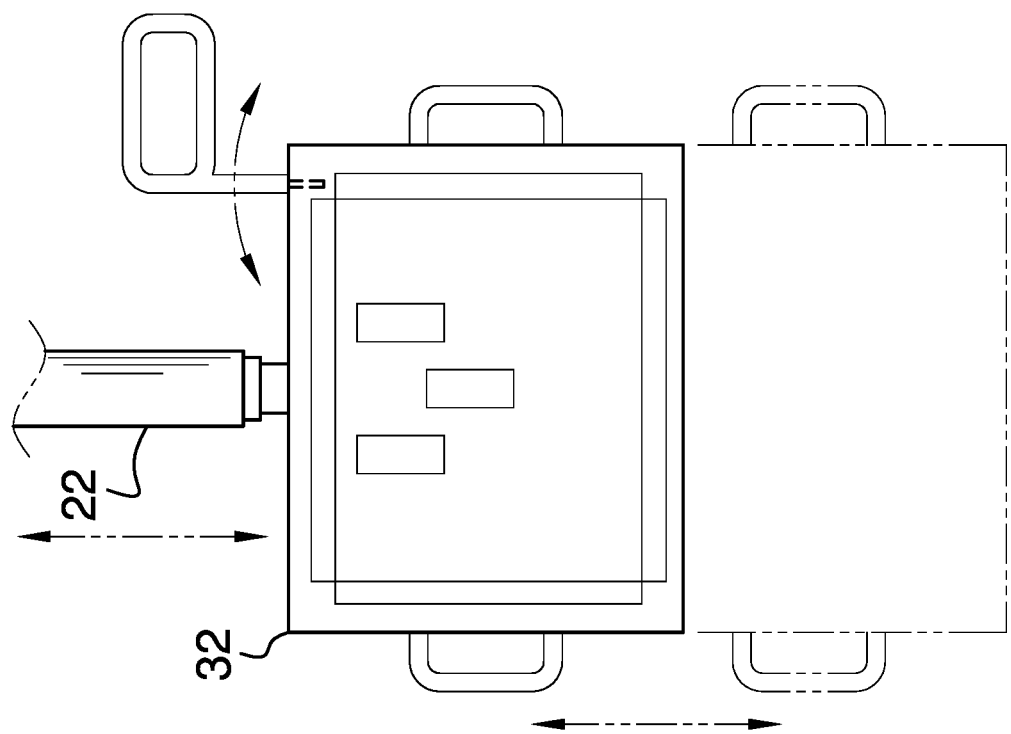
FIG. 3 is a front view of an X-ray detection panel of an embodiment of the disclosure.
Figure 2:
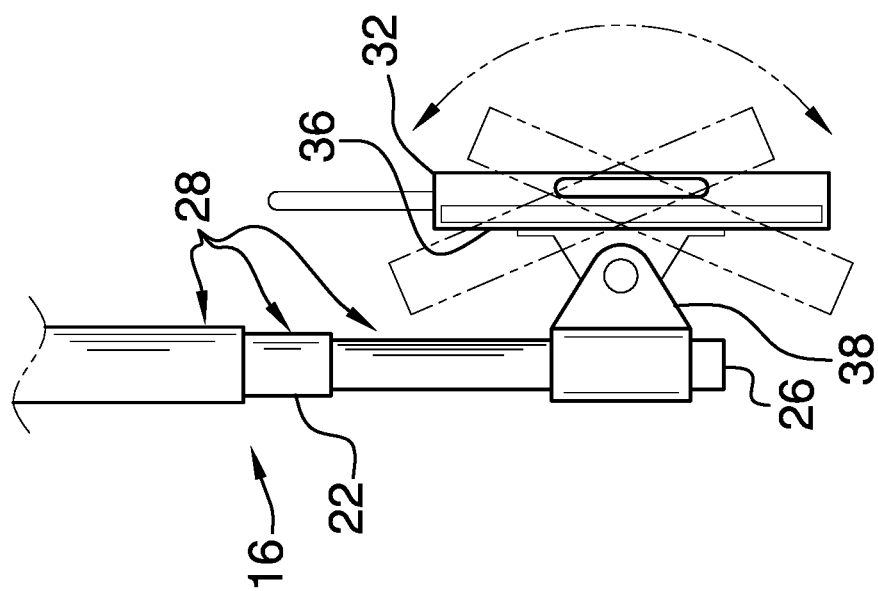
FIG. 2 is a perspective view of an X-ray detection panel of an embodiment of the disclosure.
Figure 5:
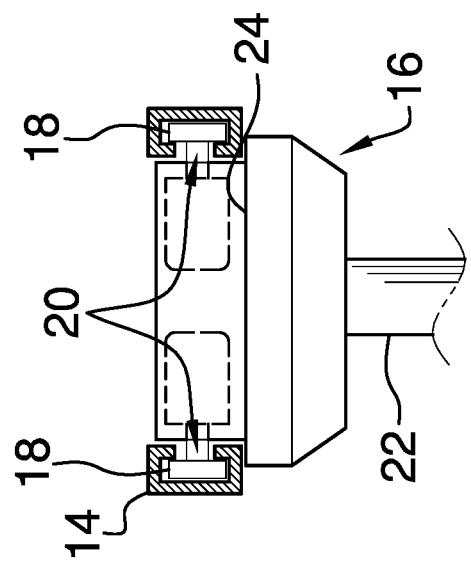
FIG. 5 is a cut-away view of a plurality of rollers of an embodiment of the disclosure.
Figure 4:
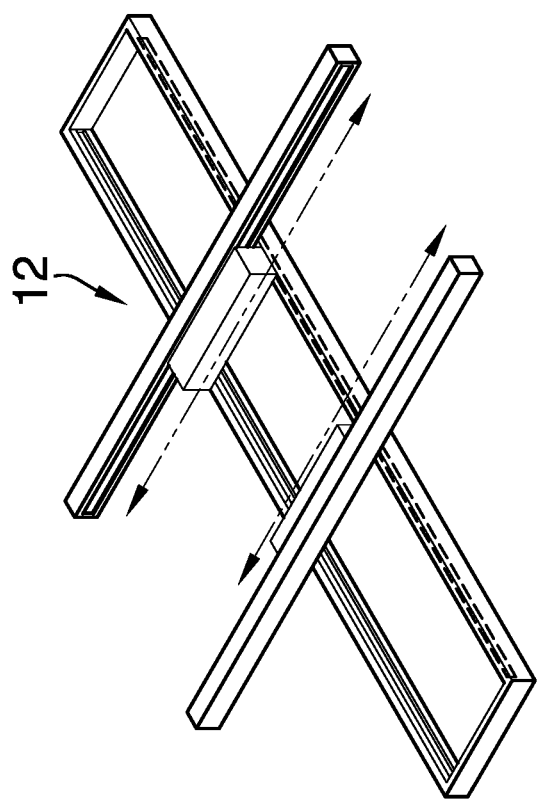
FIG. 4 is a perspective view of an existing X-ray track unit as described in an embodiment of the disclosure.

With reference now to the drawings, and in particular to FIGS. 1 through 5 thereof, a new movable bucky device embodying the principles and concepts of an embodiment of the disclosure and generally designated by the reference numeral 10 will be described.

As best illustrated in FIGS. 1 through 5, the movable X-ray bucky assembly 10 generally comprises an X-ray track unit 12 that is mounted to a ceiling 13 of an X-ray room. The X-ray room may be an X-ray room in a hospital, clinic or any other medical facility that employs an X-ray machine. The X-ray track unit 12 includes a positioning rail 14 is that is slidable along a lateral axis of the X-ray track unit 12. The X-ray track unit 12 may be a track unit conventional to any existing X-ray machine.

An X-ray bucky mount 16 is provided and the X-ray bucky mount 16 is movably coupled to the positioning rail 14. Additionally, the X-ray bucky mount 16 is movable along a longitudinal axis of the positioning rail 14 and the longitudinal axis is oriented perpendicular to the lateral axis of the X-ray track unit 12. In this way the X-ray bucky mount 16 can be positionable at plurality of locations in the X-ray room in the same manner as existing X-ray emitters on conventional X-ray machines.

The X-ray bucky mount 16 comprises a plurality of rollers 18 that each rollably engages a respective channel 20 in the positioning rail 14. The rollers 18 may be alternatively designed to accommodate the design of the track unit of any existing X-ray machine. The X-ray bucky mount 16 further includes a tube 22 that has a first end 24 and a second end 26. Each of the rollers 18 is coupled to the tube 22 and is positioned adjacent to the first end 24 such that the tube 22 extends downwardly from the positioning rail 14 in a vertical orientation. Moreover, the rollers 18 are positioned on opposite sides of the tube 22 with respect to each other thereby facilitating the tube 22 to transfer weight into the positioning rail 14. The tube 22 comprises a plurality of sections 28 each slidably receiving each other such that the tube 22 has a telescopically adjustable length.

A receiver 30 is coupled to the tube 22 and the receiver 30 is oriented to extend laterally away from the tube 22. The receiver 30 is positioned adjacent to the second end 26 of the tube 22. The receiver 30 may comprise a pair of panels that are spaced apart from each other on the tube 22, or any other mechanical coupler that is capable of receiving a pivoting coupling. An X-ray detection panel 32 is pivotally coupled to the X-ray bucky mount 16 thereby facilitating the X-ray detection panel 32 to be positioned adjacent to a patient 34 regardless of the position of the patient 34 within the X-ray room. In this way an X-ray image can be taken of the patient 34 when the patient 34 is not able to stand in front of a conventional wall mounted X-ray detection panel.

The X-ray detection panel 32 may be a Bucky-Potter grid of any conventional design and the X-ray detection panel 32 has a rear surface 36. The rear surface 36 is pivotally coupled to the receiver 30. In this way the rear surface 36 of the X-ray panel is positionable at a selected angle with respect to an axis extending through the first 24 and second 26 ends of the tube 22. Thus, the X-ray detection panel 32 can be aligned with the patient 34 regardless of the patient's 34 physical orientation and position within the X-ray room.

In use, the X-ray bucky mount 16 is slid along the X-ray track unit 12 in order to position the X-ray detection panel 32 adjacent to the patient 34. In this way The X-ray bucky mount 16 can be positioned near a patient 34 that is not physically capable of standing next to a conventional, wall mounted X-ray panel. Additionally, the X-ray detection panel 32 is oriented on the receiver 30 for exposure to X-rays emitted by an X-ray emitter in the conventional means of capturing an X-ray image for medical diagnostic purposes. In this way a chest X-ray, or the like, can be captured of the patient 34 even though the patient 34 may not be capable of positioning themselves in the conventional posture for a chest X-ray.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A movable X-ray bucky assembly being movably mounted onto an existing X-ray track system wherein said assembly is configured to be positioned at any location in an X-ray room, said assembly comprising:
   an X-ray track unit being mounted to a ceiling of an X-ray room, said X-ray track unit including a positioning rail being slidable along a lateral axis of said X-ray track unit;
   a X-ray bucky mount being movably coupled to said positioning rail independent to an X-ray emitter mounted to said X-ray track unit, said X-ray bucky mount being movable independently relative to the X-ray emitter along a longitudinal axis of said positioning rail, said longitudinal axis being oriented perpendicular to said lateral axis of said X-ray track unit wherein said X-ray bucky mount is configured to be positionable at plurality of locations in the X-ray room; and
   an X-ray detection panel being pivotally coupled to said X-ray bucky mount wherein said X-ray detection panel is configured to be positioned adjacent to a patient regardless of the position of the patient within the X-ray room thereby facilitating an X-ray image to be taken of the patient when the patient is not able to stand in front of a conventional wall mounted X-ray detection panel.

2. The assembly according to claim 1, wherein said X-ray bucky mount comprises:
   a plurality of rollers, each of said rollers rollably engaging a respective channel in said positioning rail;
   a tube having a first end and a second end, each of said rollers being coupled to said tube and being positioned adjacent to said first end such that said tube extends downwardly from said positioning rail in a vertical orientation; and
   said rollers being positioned on opposite sides of said tube with respect to each other thereby facilitating said tube to transfer weight into said positioning rail.

3. The assembly according to claim 2, wherein:
   said tube comprises a plurality of sections each slidably receiving each other such that said tube has a telescopically adjustable length; and
   said X-ray bucky mount includes a receiver being coupled to said tube.

4. The assembly according to claim 3, wherein said receiver is oriented to extend laterally away from said tube, said receiver being positioned adjacent to said second end of said tube.

5. The assembly according to claim 3, wherein said X-ray detection panel has a rear surface, said rear surface being pivotally coupled to a receiver such that said rear surface of said X-ray panel is positionable at a selected angle with respect to an axis extending through said first and second ends of said tube.

6. A movable X-ray bucky assembly being movably mounted onto an existing X-ray track system wherein said assembly is configured to be positioned at any location in an X-ray room, said assembly comprising:
   an X-ray track unit being mounted to a ceiling of an X-ray room, said X-ray track unit including a positioning rail being slidable along a lateral axis of said X-ray track unit;
   a X-ray bucky mount being movably coupled to said positioning rail independent to an X-ray emitter mounted to said X-ray track unit, said X-ray bucky mount being movable independently relative to the X-ray emitter along a longitudinal axis of said positioning rail, said longitudinal axis being oriented perpendicular to said lateral axis of said X-ray track unit wherein said X-ray bucky mount is configured to be positionable at plurality of locations in the X-ray room, said X-ray bucky mount comprising:
      a plurality of rollers, each of said rollers rollably engaging a respective channel in said positioning rail;
      a tube having a first end and a second end, each of said rollers being coupled to said tube and being positioned adjacent to said first end such that said tube extends downwardly from said positioning rail in a vertical orientation, said rollers being positioned on opposite sides of said tube with respect to each other thereby facilitating said tube to transfer weight into said positioning rail, said tube comprising a plurality of sections each slidably receiving each other such that said tube has a telescopically adjustable length; and a receiver being coupled to said tube, said receiver being oriented to extend laterally away from said tube, said receiver being positioned adjacent to said second end of said tube; and an X-ray detection panel being pivotally coupled to said X-ray bucky mount wherein said X-ray detection panel is configured to be positioned adjacent to a patient regardless of the position of the patient within the X-ray room thereby facilitating an X-ray image to be taken of the patient when the patient is not able to stand in front of a conventional wall mounted X-ray detection panel, said X-ray detection panel having a rear surface, said rear surface being pivotally coupled to said receiver such that said rear surface of said X-ray panel is positionable at a selected angle with respect to an axis extending through said first and second ends of said tube.

\* \* \* \* \*